United States Patent [19]

Higuchi et al.

[11] Patent Number: 5,514,587
[45] Date of Patent: May 7, 1996

[54] DNA FRAGMENT ENCODING A HYDROGEN PEROXIDE-GENERATING NADH OXIDASE

[75] Inventors: Masako Higuchi, Neyagawa; Junichi Matsumoto, Moriguchi; Yoshikazu Yamamoto, Neyagawa; Yoshiyuki Kamio, Sendai; Kazuo Izaki, Miyagi, all of Japan

[73] Assignee: Nippon Paint Co., Ltd., Osaka, Japan

[21] Appl. No.: 220,677

[22] Filed: Mar. 31, 1994

[30] Foreign Application Priority Data

Mar. 31, 1993 [JP] Japan ..................... 5-073989
Oct. 12, 1993 [JP] Japan ..................... 5-254459

[51] Int. Cl.⁶ .............. C12N 1/20; C12N 9/06; C12N 15/00; C07H 21/04
[52] U.S. Cl. ............. 435/320.1; 435/191; 435/252.3; 536/23.2; 536/24.1
[58] Field of Search ............. 435/191, 252.3, 435/320.1; 536/23.2, 24.1

[56] References Cited

FOREIGN PATENT DOCUMENTS

| | | |
|---|---|---|
| 0385415 | 9/1990 | European Pat. Off. |
| 3725851 | 2/1988 | Germany. |
| 4221830 | 1/1993 | Germany. |
| 04365478 | 12/1992 | Japan. |
| 5344890 | 12/1993 | Japan. |

OTHER PUBLICATIONS

"Molecular Cloning And Sequence Analysis Of The Gene Encoding The H2O2–Forming NADH Oxidase From Streptococcus Mutans"; Abstract; Feb. 11, 1994; Higuchi, et al.; Database EMBL.

"Identification of Two Distinct NADH Oxidases Corresponding to H2O2–forming Oxidase Induced in Streptococcus Mutans"; J. Gen. Microbiology; pp. 2343–2351; vol. 139, No. PT10; Oct. 1993.

Higuchi (1992) Oral Microbiol. Immunol. 7:309–314, Park, et al. (1992) Eur. J. Biochem. 205(3):875–879.

Primary Examiner—Robert A. Wax
Assistant Examiner—Lisa J. Hobbs
Attorney, Agent, or Firm—Townsend & Banta

[57] ABSTRACT

A gene encoding a hydrogen peroxide-generating NADH oxidase and a method for preparing a large amount of the NADH oxidase with the use of the gene and gene recombinant techniques are disclosed.

5 Claims, No Drawings

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 1809 base pairs
        ( B ) TYPE: nucleic acid
        ( C ) STRANDEDNESS: doubule
        ( D ) TOPOLOGY: linear ( i i ) MOLECULE TYPE: genomic DNA ( i i i ) HYPOTHETICAL: No (iv) ANTI-SENSE: No (v) ORIGINAL SOURCE:
   (B) STRAIN:Streptococcus mutans NCIB11723

(vi) SEQUENCE DESCRIPTION: SEQ ID NO: 1:

| | | | | | | |
|---|---|---|---|---|---|---|
| GGATCCCTTC | TCATGTTCTC | TCACAAGGAT | TTGAGGTTTT | AGGTGAAGAT | GGTTTAGCAC | 60 |
| AACGTGGAAC | CTTTATTGTA | GATCCGGATG | GTATCATTCA | AATGATGGAA | GTCAATGCAG | 120 |
| ATGGTATTGG | TCGTGATGCT | AGTACCTTGA | TTGATAAAGT | TCGTGCAGCT | CAATCTATTC | 180 |
| GCCAACATCC | AGGAGAAGTT | TGCCCTGCCA | AATGGAAAGA | GGGAGCTGAA | ACTTTAAAAC | 240 |
| CAAGTTTGGT | ACTTGTCGGT | AAAATTTAAG | GAGAAACTAT | GGCATTAGAC | GCAGAAATCA | 300 |
| AAGAGCAGTT | AGGACAGTAT | CTTCAATTAC | TTGAGTGTGA | GATTGTTTTA | CAAGCTCAAT | 360 |
| TAAAAGACGA | TGCTAATTCT | CAAAAAGTTA | AGGAATTTCT | CCAAGAAATC | GTTGCAATGT | 420 |
| CTCCTATGAT | TTCTTTAGAC | GAAAAGGAAC | TTCCGCGAAC | ACCTAGTTTT | CGCATAGCTA | 480 |
| AAAAGGGGCA | AGAATCTGGT | GTTGAATTTG | CTGGCTTACC | CCTTGGTCAC | GAATTTTACT | 540 |
| TCGTTTATCT | TGGCTCTGTT | ACAGGTTTCA | GGGCGTCCGC | TAAGGTAGAG | ACTGATATTG | 600 |
| TCAAACGCAT | TCAAGCTGTT | GATGAACCTA | TGCATTTTGA | AACCTATGTT | AGTTTGACTT | 660 |
| GTCATAATTG | TCCAGATGTT | GTTCAGGCTT | TCAATATCAT | GTCAGTTGTT | AATCCCAACA | 720 |
| TTTCACATAC | AATGGTGGAA | GGTGGCATGT | TTAAAGATGA | AATTGAAGCT | AAGGGAATTA | 780 |
| TGTCTGTGCC | AACTGTCTAT | AAAGATGGAA | CAGAATTTAC | CTCAGGGCGT | GCTAGCATAG | 840 |
| AGCAATTACT | AGACTTGATA | GCAGGTCCTC | TTAAAGAAGA | TGCTTTTGAT | GATAAAGGTG | 900 |
| TTTTTGATGT | CCTTGTTATT | GGTGGGGGTC | CTGCTGGTAA | TAGCGCGGCT | ATCTATGCTG | 960 |
| CAAGAAAGGG | AGTTAAAACA | GGACTTTTAG | CTGAAACCAT | GGGTGGTCAA | GTTATGGAAA | 1020 |
| CCGTGGGTAT | TGAAAATATG | ATCGGTACCC | CATATGTTGA | AGGACCCCAA | TTAATGGCTC | 1080 |
| AGGTGGAAGA | GCATACCAAG | TCTTATTCTG | TTGACATCAT | GAAGGCACCG | CGTGCTAAGT | 1140 |
| CTATTCAAAA | GACAGACTTG | GTTGAAGTTG | AACTTGATAA | TGGAGCTCAT | TTGAAAGCAA | 1200 |
| AGACAGCTGT | TTTGGCCTTA | GGTGCCAAGT | GGCGTAAAAT | CAATGTACCA | GGAGAAAAAG | 1260 |
| AATTCTTTAA | TAAAGGTGTT | ACTTACTGTC | CGCACTGTGA | TGGTCCTCTT | TTCACAGACA | 1320 |
| AAAAGTCGC | TGTCATTGGC | GGTGGAAACT | CAGGTTTAGA | AGCAGCTATT | GATTTGGCTG | 1380 |
| GGTTAGCTAG | CCATGTCTAT | ATTTTAGAAT | TTTTACCTGA | GTTAAAAGCT | GATAAGATCT | 1440 |
| TACAAGATCG | TGCGGAAGCT | CTTGATAATA | TTACCATTCT | AACTAATGTT | GCGACTAAAG | 1500 |
| AAATTATTGG | CAATGACCAC | GTAGAAGGTC | TTCGTTACAG | TGATCGTACG | ACCAATGAAG | 1560 |
| AGTACTTGCT | TGATTAGAA | GGTGTTTTTG | TTCAAATTGG | ATTGGTACCT | AGTACTGACT | 1620 |
| GGTTAAAGGA | TAGTGGACTA | GCACTCAATG | AAAAAGGTGA | AATCATTGTT | GCTAAAGATG | 1680 |
| GCGCAACTAA | TATTCCTGCT | ATTTTTGCAG | CTGGTGATTG | CACAGATAGT | GCCTACAAAC | 1740 |
| AAATTATCAT | TTCCATGGGT | TCTGGAGCTA | CTGCGGCTTT | AGGTGCCTTT | GATTATTTGA | 1800 |
| TTAGAAATT | | | | | | 1809 |

(2) INFORMATION FOR SEQ ID NO:2:

(i) SEQUENCE CHARACTERISTICS:
       (A) LENGTH: 510 amino acids
       (B) TYPE: amino acids
       (D) TOPOLOGY: linear (ii) MOLECULE TYPE: protein ( i i i ) HYPOTHETICAL: No ( i v ) ANTI-SENSE: No ( v ) ORIGINAL SOURCE:
    ( B ) STRAIN: Streptococcus mutans NCIB11723

( v i ) SEQUENCE DESCRIPTION: SEQ ID NO: 2:

| Met 1 | Ala | Leu | Asp | Ala 5 | Glu | Ile | Lys | Glu | Gln 10 | Leu | Gly | Gln | Tyr | Leu 15 |
|---|---|---|---|---|---|---|---|---|---|---|---|---|---|---|
| Gln | Leu | Leu | Glu | Cys 20 | Glu | Ile | Val | Leu | Gln 25 | Ala | Gln | Leu | Lys | Asp 30 |
| Asp | Ala | Asn | Ser | Gln 35 | Lys | Val | Lys | Glu | Phe 40 | Leu | Gln | Glu | Ile | Val 45 |
| Ala | Met | Ser | Pro | Met 50 | Ile | Ser | Leu | Asp | Glu 55 | Lys | Glu | Leu | Pro | Arg 60 |
| Thr | Pro | Ser | Phe | Arg 65 | Ile | Ala | Lys | Lys | Gly 70 | Gln | Glu | Ser | Gly | Val 75 |
| Glu | Phe | Ala | Gly | Leu 80 | Pro | Leu | Gly | His | Glu 85 | Phe | Tyr | Phe | Val | Tyr 90 |
| Leu | Gly | Ser | Val | Thr 95 | Gly | Phe | Arg | Ala | Ser 100 | Ala | Lys | Val | Glu | Thr 105 |
| Asp | Ile | Val | Lys | Arg 110 | Ile | Gln | Ala | Val | Asp 115 | Glu | Pro | Met | His | Phe 120 |
| Glu | Thr | Tyr | Val | Ser 125 | Leu | Thr | Cys | His | Asn 130 | Cys | Pro | Asp | Val | Val 135 |
| Gln | Ala | Phe | Asn | Ile 140 | Met | Ser | Val | Val | Asn 145 | Pro | Asn | Ile | Ser | His 150 |
| Thr | Met | Val | Glu | Gly 155 | Gly | Met | Phe | Lys | Asp 160 | Glu | Ile | Glu | Ala | Lys 165 |
| Gly | Ile | Met | Ser | Val 170 | Pro | Thr | Val | Tyr | Lys 175 | Asp | Gly | Thr | Glu | Phe 180 |
| Thr | Ser | Gly | Arg | Ala 185 | Ser | Ile | Glu | Gln | Leu 190 | Leu | Asp | Leu | Ile | Ala 195 |
| Gly | Pro | Leu | Lys | Glu 200 | Asp | Ala | Phe | Asp | Asp 205 | Lys | Gly | Val | Phe | Asp 210 |
| Val | Leu | Val | Ile | Gly 215 | Gly | Gly | Pro | Ala | Gly 220 | Asn | Ser | Ala | Ala | Ile 225 |
| Tyr | Ala | Ala | Arg | Lys 230 | Gly | Val | Lys | Thr | Gly 235 | Leu | Leu | Ala | Glu | Thr 240 |
| Met | Gly | Gly | Gln | Val 245 | Met | Glu | Thr | Val | Gly 250 | Ile | Glu | Asn | Met | Ile 255 |
| Gly | Thr | Pro | Tyr | Val 260 | Glu | Gly | Pro | Gln | Leu 265 | Met | Ala | Gln | Val | Glu 270 |
| Glu | His | Thr | Lys | Ser 275 | Tyr | Ser | Val | Asp | Ile 280 | Met | Lys | Ala | Pro | Arg 285 |
| Ala | Lys | Ser | Ile | Gln 290 | Lys | Thr | Asp | Leu | Val 295 | Glu | Val | Glu | Leu | Asp 300 |
| Asn | Gly | Ala | His | Leu 305 | Lys | Ala | Lys | Thr | Ala 310 | Val | Leu | Ala | Leu | Gly 315 |
| Ala | Lys | Trp | Arg | Lys 320 | Ile | Asn | Val | Pro | Gly 325 | Glu | Lys | Glu | Phe | Phe 330 |
| Asn | Lys | Gly | Val | Thr 335 | Tyr | Cys | Pro | His | Cys 340 | Asp | Gly | Pro | Leu | Phe 345 |
| Thr | Asp | Lys | Lys | Val 350 | Ala | Val | Ile | Gly | Gly 355 | Gly | Asn | Ser | Gly | Leu 360 |

| | | | | | | | | | | | | | |
|---|---|---|---|---|---|---|---|---|---|---|---|---|---|
| Glu | Ala | Ala | Ile | Asp 365 | Leu | Ala | Gly | Leu | Ala 370 | Ser | His | Val | Tyr | Ile 375 |
| Leu | Glu | Phe | Leu | Pro 380 | Glu | Leu | Lys | Ala | Asp 385 | Lys | Ile | Leu | Gln | Asp 390 |
| Arg | Ala | Glu | Ala | Leu 395 | Asp | Asn | Ile | Thr | Ile 400 | Leu | Thr | Asn | Val | Ala 405 |
| Thr | Lys | Glu | Ile | Ile 410 | Gly | Asn | Asp | His | Val 415 | Glu | Gly | Leu | Arg | Tyr 420 |
| Ser | Asp | Arg | Thr | Thr 425 | Asn | Glu | Glu | Tyr | Leu 430 | Leu | Asp | Leu | Glu | Gly 435 |
| Val | Phe | Val | Gln | Ile 440 | Gly | Leu | Val | Pro | Ser 445 | Thr | Asp | Trp | Leu | Lys 450 |
| Asp | Ser | Gly | Leu | Ala 455 | Leu | Asn | Glu | Lys | Gly 460 | Glu | Ile | Ile | Val | Ala 465 |
| Lys | Asp | Gly | Ala | Thr 470 | Asn | Ile | Pro | Ala | Ile 475 | Phe | Ala | Ala | Gly | Asp 480 |
| Cys | Thr | Asp | Ser | Ala 485 | Tyr | Lys | Gln | Ile | Ile 490 | Ile | Ser | Met | Gly | Ser 495 |
| Lys | Ala | Thr | Ala | Ala 500 | Leu | Gly | Ala | Phe | Asp 505 | Tyr | Leu | Ile | Arg | Asn 510 |

DNA FRAGMENT ENCODING A HYDROGEN PEROXIDE-GENERATING NADH OXIDASE

BACKGROUND OF THE INVENTION

1. Field of the Invention

The present invention relates to a DNA fragment encoding an enzyme that catalyzes the reaction in which NADH is oxidized by oxygen molecules to generate hydrogen peroxide (Japanese Laid-Open Publication 2-407889) and a method for preparing the enzyme with the use of a microorganism including a plasmid containing the fragment. The enzyme is useful for detection of a very small amount of substance in vivo with the use of the reaction generating NADH.

2. Description of the Prior Art

NADH oxidases are divided into two groups, one group which generates hydrogen peroxide (hydrogen peroxide-generating enzymes) and the other group which generates water (water-generating enzymes) by the reaction with oxygen molecules.

Hydrogen peroxide-generating enzymes can be found in a culture of *Streptococus mutans*. However, it is difficult to obtain a stable culture condition in which water-generating enzymes can be obtained in a much higher level than the level of hydrogen peroxide-generating enzymes, which can also be found in the culture. Moreover, it is necessary to separate hydrogen peroxide generating enzymes from water-generating enzymes in the culture. Therefore, a method for preparing a large amount of hydrogen peroxide-generating NADH oxidases stably in a rational way, i.e., a method for preparing NADH oxidases with the use of gene recombinant techniques is desired.

The conventional method for preparing NADH oxidases with a culture of *Streptococus mutans* is not suitable for obtaining a large amount of a hydrogen peroxide-generating NADH oxidase. Therefore, one of the objectives of the present invention is to provide a gene encoding a NADH oxidase, which can be used in a method for preparing a large amount of a hydrogen peroxide-generating NADH oxidase by gene recombinant techniques.

SUMMARY OF THE INVENTION

As the result of our researches to develop a method for preparing a hydrogen peroxide-generating NADH oxidase, we have eventually cloned a gene encoding hydrogen peroxide-generating NADH oxidase derived from *Streptococus mutans* and sequenced the gene.

The present invention, provides a DNA fragment encoding the hydrogen peroxide-generating NADH oxidase.

The present invention also provides a DNA fragment that encodes a protein containing a NADH binding site of the NADH oxidase having the following amino acid sequence:

| Val | Leu | Val | Ile | Gly | Gly | Gly | Pro | Ala | Gly | Asn | Ser |
| Ala | Ala | Ile | Tyr | Ala | Ala | Arg | Lys | Gly | Val | Lys | Thr |

The present invention provides a DNA fragment of following base sequence that encodes a protein containing a NADH binding site of the NADH oxidase:

| GTCCTTGTTA | TTGGTGGGGG | TCCTGCTGGT | AATAGCGCGG |
| CTATCTATGC | TGCAAGAAAG | GGAGTTAAAA | CA |

The present invention also provides a DNA fragment encoding a protein containing a FAD binding site of the NADH oxidase having the following amino acid sequence:

| Val | Ala | Val | Ile | Gly | Gly | Gly | Asn | Ser | Gly | Leu | Glu |
| Ala | Ala | Ile | Asp | Leu | Ala | Gly | Leu | Ala | Ser | His | Val |
| Tyr | | | | | | | | | | | |

The present invention provides a DNA fragment of the following base sequence which encodes a protein containing a FAD binding site of the NADH oxidase:

| GTCGCTGTCA | TTGGCGGTGG | AAACTCAGGT | TTAGAAGCAG |
| TCATTGATTT | GGCTGGGTTA | GCTAGCCATG | TCTAT |

The present invention also provides a DNA fragment of following base sequence which encodes the NADH oxidase:

| | | | | AT | GGCATTAGAC | GCAGAAATCA |
|---|---|---|---|---|---|---|
| AAGAGCAGTT | AGGACAGTAT | CTTCAATTAC | TTGAGTGTGA | GATTGTTTTA | CAAGCTCAAT |
| TAAAAGACGA | TGCTAATTCT | CAAAAAGTTA | AGGAATTTCT | CCAAGAAATC | GTTGCAATGT |
| CTCCTATGAT | TTCTTTAGAC | GAAAAGGAAC | TTCCGCGAAC | ACCTAGTTTT | CGCATAGCTA |
| AAAAGGGGCA | AGAATCTGGT | GTTGAATTTG | CTGGCTTACC | CCTTGGTCAC | GAATTTTACT |
| TCGTTTATCT | TGGCTCTGTT | ACAGGTTTCA | GGGCGTCCGC | TAAGGTAGAG | ACTGATATTG |
| TCAAACGCAT | TCAAGCTGTT | GATGAACCTA | TGCATTTTGA | AACCTATGTT | AGTTTGACTT |
| GTCATAATTG | TCCAGATGTT | GTTCAGGCTT | TCAATATCAT | GTCAGTTGTT | AATCCCAACA |
| TTTCACATAC | AATGGTGGAA | GGTGGCATGT | TTAAAGATGA | AATTGAAGCT | AAGGGAATTA |
| TGTCTGTGCC | AACTGTCTAT | AAAGATGGAA | CAGAATTTAC | CTCAGGGCGT | GCTAGCATAG |
| AGCAATTACT | AGACTTGATA | GCAGGTCCTC | TTAAAGAAGA | TGCTTTTGAT | GATAAAGGTG |
| TTTTTGATGT | CCTTGTTATT | GGTGGGGGTC | CTGCTGGTAA | TAGCGCGGCT | ATCTATGCTG |
| CAAGAAAGGG | AGTTAAAACA | GGACTTTTAG | CTGAAACCAT | GGGTGGTCAA | GTTATGGAAA |
| CCGTGGGTAT | TGAAAATATG | ATCGGTACCC | CATATGTTGA | AGGACCCCAA | TTAATGGCTC |
| AGGTGGAAGA | GCATACCAAG | TCTTATTCTG | TTGACATCAT | GAAGGCACCG | CGTGCTAAGT |
| CTATTCAAAA | GACAGACTTG | GTTGAAGTTG | AACTTGATAA | TGGAGCTCAT | TTGAAAGCAA |
| AGACAGCTGT | TTTGGCCTTA | GGTGCCAAGT | GGCGTAAAAT | CAATGTACCA | GGAGAAAAAG |
| AATTCTTTAA | TAAAGGTGTT | ACTTACTGTC | CGCACTGTGA | TGGTCCTCTT | TTCACAGACA |
| AAAAAGTCGC | TGTCATTGGC | GGTGGAAACT | CAGGTTTAGA | AGCAGCTATT | GATTTGGCTG |
| GGTTAGCTAG | CCATGTCTAT | ATTTTAGAAT | TTTTACCTGA | GTTAAAAGCT | GATAAGATCT |
| TACAAGATCG | TGCGGAAGCT | CTTGATAATA | TTACCATTCT | AACTAATGTT | GCGACTAAAG |
| AAATTATTGG | CAATGACCAC | GTAGAAGGTC | TTCGTTACAG | TGATCGTACG | ACCAATGAAG |
| AGTACTTGCT | TGATTAGAA | GGTGTTTTG | TTCAAATTGG | ATTGGTACCT | AGTACTGACT |
| GGTTAAAGGA | TAGTGGACTA | GCACTCAATG | AAAAAGGTGA | AATCATTGTT | GCTAAAGATG |
| GCGCAACTAA | TATTCCTGCT | ATTTTTGCAG | CTGGTGATTG | CACAGATAGT | GCCTACAAAC |
| AAATTATCAT | TTCCATGGGT | TCTGGAGCTA | CTGCGGCTTT | AGGTGCCTTT | GATTATTTGA |
| TTAGAAATT// | | | | | |

The present invention also provides a DNA fragment encoding the NADH oxidase having the following amino acid sequence:

| | | | | | | | | | | | | | | | |
|---|---|---|---|---|---|---|---|---|---|---|---|---|---|---|---|
| Met | Ala | Leu | Asp | Ala | Glu | Ile | Lys | Glu | Gln | Leu | Gly | Gln | Tyr | Leu | 15 |
| Gln | Leu | Leu | Glu | Cys | Glu | Ile | Val | Leu | Ala | Gln | Leu | Lys | Asp | 30 |
| Asp | Ala | Asn | Ser | Gln | Lys | Val | Lys | Glu | Phe | Leu | Gln | Glu | Ile | Val | 45 |
| Ala | Met | Ser | Pro | Met | Ile | Ser | Leu | Asp | Glu | Lys | Glu | Leu | Pro | Arg | 60 |
| Thr | Pro | Ser | Phe | Arg | Ile | Ala | Lys | Lys | Gly | Gln | Glu | Ser | Gly | Val | 75 |
| Glu | Phe | Ala | Gly | Leu | Pro | Leu | Gly | His | Glu | Phe | Tyr | Phe | Val | Tyr | 90 |
| Leu | Gly | Ser | Val | Thr | Gly | Phe | Arg | Ala | Ser | Ala | Lys | Val | Glu | Thr | 105 |
| Asp | Ile | Val | Lys | Arg | Ile | Gln | Ala | Val | Asp | Glu | Pro | Met | His | Phe | 120 |
| Glu | Thr | Tyr | Val | Ser | Leu | Thr | Cys | His | Asn | Cys | Pro | Asp | Val | Val | 135 |
| Gln | Ala | Phe | Asn | Ile | Met | Ser | Val | Val | Asn | Pro | Asn | Ile | Ser | His | 150 |
| Thr | Met | Val | Gln | Ile | Gly | Gly | Met | Phe | Lys | ASp | Ile | Glu | Ala | Lys | 165 |
| Gly | Ile | Met | Ser | Val | Pro | Thr | Val | Tyr | Lys | Asp | Gly | Thr | Glu | Phe | 180 |
| Thr | Ser | Gly | Arg | Ala | Ser | Ile | Glu | Gln | Leu | Leu | Asp | Leu | Ile | Ala | 195 |
| Gly | Pro | Leu | Lys | Glu | Asp | Ala | Phe | Asp | Asp | Lys | Gly | Val | Phe | Asp | 210 |
| Val | Leu | Val | Ile | Gly | Gly | Gly | Pro | Ala | Gly | Asn | Ser | Ala | Ala | Ile | 225 |
| Tyr | Ala | Ala | Arg | Lys | Gly | Val | Lys | Thr | Gly | Leu | Leu | Ala | Glu | Thr | 240 |
| Met | Gly | Gly | Gln | Val | Met | Glu | Thr | Val | Gly | Ile | Glu | Asn | Met | Ile | 255 |
| Gly | Thr | Pro | Tyr | Val | Glu | Gly | Pro | Gln | Leu | Met | Ala | Gln | Val | Glu | 270 |
| Glu | His | Thr | Lys | Ser | Tyr | Ser | Val | Asp | Ile | Met | Lys | Ala | Pro | Arg | 285 |
| Ala | Lys | Ser | Ile | Gln | Lys | Thr | Asp | Leu | Val | Glu | Val | Glu | Leu | Asp | 300 |
| Asn | Gly | Ala | His | Leu | Lys | Ala | Lys | Thr | Ala | Val | Lue | Ala | Lue | Gly | 315 |
| Ala | Lys | Trp | Arg | Lys | Ile | Asn | Val | Pro | Gly | Glu | Lys | Glu | Phe | Phe | 330 |
| Asn | Lys | Gly | Val | Thr | Tyr | Cys | Pro | His | Cys | Asp | Gly | Pro | Leu | Phe | 345 |
| Thr | Asp | Lys | Lys | Val | Ala | Val | Ile | Gly | Gly | Gly | Asn | Ser | Gly | Leu | 360 |
| Glu | Ala | Ala | Ile | Asp | Leu | Ala | Gly | Leu | Ala | Ser | His | Val | Tyr | Ile | 375 |
| Leu | Glu | Phe | Leu | Pro | Glu | Leu | Lys | Ala | Asp | Lys | Ile | Leu | Gln | Asp | 390 |
| Arg | Ala | Glu | Ala | Lue | Asp | Asn | Ile | Thr | Ile | Leu | Thr | Asn | Val | Ala | 405 |
| Thr | Lys | Glu | Ile | Ile | Gly | Asn | Asp | His | Val | Glu | Gly | Leu | Arg | Tyr | 420 |
| Ser | Asp | Arg | Thr | Thr | Asn | Glu | Glu | Tyr | Leu | Leu | Asp | Leu | Glu | Gly | 435 |
| Val | Phe | Val | Gln | Ile | Gly | Leu | Val | Pro | Ser | Thr | Asp | Trp | Leu | Lys | 450 |
| Asp | Ser | Gly | Leu | Ala | Leu | Asn | Glu | Lys | Gly | Glu | Ile | Ile | Val | Ala | 465 |
| Lys | Asp | Gly | Ala | Thr | Asn | Ile | Pro | Ala | Ile | Phe | Ala | Ala | Gly | Asp | 480 |
| Cys | Thr | Asp | Ser | Ala | Tyr | Lys | Gln | Ile | Ile | Ile | Ser | Met | Gly | Ser | 495 |
| Lys | Ala | Thr | Ala | Ala | Leu | Gly | Ala | Phe | Asp | Tyr | Leu | Ile | Arg | Asn | 510 |
| * | | | | | | | | | | | | | | | |

In the upstream region of the DNA fragment of the present invention may be a non-translational region having the following base sequence:

| | | | | | | |
|---|---|---|---|---|---|---|
| GGATCCCTTC | TCATGTTCTC | TCACAAGGAT | TTGAGGTTTT | AGGTGAAGAT | GGTTTAGCAC | 60 |
| AACGTGGAAC | CTTTATTGTA | GATCCGGATG | GTATCATTCA | AATGATGGAA | GTCAATGCAG | 120 |
| ATGGTATTGG | TCGTGATGCT | AGTACCTTGA | TTGATAAAGT | TCGTGCAGCT | CAATCTATTC | 180 |
| GCCAACATCC | AGGAGAAGTT | TGCCCTGCCA | AATGGAAAGA | GGGAGCTGAA | ACTTTAAAAC | 240 |
| CAAGTTTGGT | ACTTGTCGGT | AAAATTTAAG | GAGAAACT | | | |

DETAILED DESCRIPTION OF THE PREFERRED EMBODIMENTS

The gene encoding the NADH oxidase of the present invention may be cloned by standard methods. For example, first, genomic DNA is prepared from a microorganism having an ability to produce a hydroxy peroxide-generating NADH oxidase. The prepared genomic DNA is digested with an appropriate restriction enzyme to obtain DNA fragments. A vector is also digested with the appropriate restriction enzymes. One of the obtained DNA fragments and the digested vector are ligated by the use of a T4 DNA ligase to obtain recombinant DNA.

The obtained recombinant DNAs are further treated with appropriate restriction enzymes. Then each of the treated DNA fragments is ligated into a cloning vector and the obtained recombinant vector is introduced into a host microorganism to prepare a transformant. The transformants may be screened for desired transformants by a standard method in order to clone a gene encoding the NADH oxidase.

In more detail, Streptococus mutans NCIB11723 is cultured in a medium containing appropriate amounts of carbon, nitrogen, inorganic salts, and other nutrient sources and the resulting culture is centrifuged to collect the cells. Examples of preferable mediums include a brain-heart infusion medium and the like. The temperature for culture is in the range from 20° to 40° C., preferably, from 30° to 37° C. The culture starts with pH6 to 8, preferably about 7. The culture continues until about the middle of the log growth phase by a stand culture. The DNA can be prepared from lytic cells.

Methods for lysing cells include cell treatments with cell wall-lytic enzymes, such as a lysozyme and an α-glucanase, and optionally together with other enzymes or surfactant, such as sodium lauryl sulfate.

DNA can be isolated and purified from lytic cells according to standard techniques, such as appropriate combination of phenol extraction, protein removing, protease treatment, ribonuclease treatment, alcohol precipitation, centrifugation, and the like.

Methods for cleaving DNAs include ultrasonication, restriction enzyme treatment and the like. After being cleaved, a base sequence of the terminal of a DNA fragment can be altered by the treatment with modifying enzymes, such as phosphatases and DNA polymerases.

To select DNA fragments having a base sequence encoding the desired protein, cleaved DNAs can be gel electrophoresed and subjected to Southern hybridization (Southern, E. M., J. Mol. Biol., 98, 503 (1975)) with the use of synthetic probes based on amino acid sequence of the desired protein. Positive DNA fragment(s) can be extracted from a gel to obtain appropriate length of fragment(s).

As for vectors, those derived from phages or plasmids, which can autonomously propagate in a host cell can be used. For example, λ phages, M13 phages, pBR322, pUC118, and pUC119 can be used for Escherichia coli (E. coli) host cell.

Method for ligating a DNA fragment and a vector fragment can use any methods using known DNA ligase and the like. For example, a DNA fragment and a vector fragment can be ligated in vitro with the action of an appropriate DNA ligase to prepare recombinant DNA.

As for host cell, any microorganism in which recombinant DNAs can be stably maintained and autonomically propagate, and be expressed, can be used.

Methods for introducing recombinant DNAs into host microorganism include known methods, for example, when a host microorganism is E. coli, a calcium method can be used (Lederberg. E. M., & Cohen. S. N., J. Bacteriol., 119, 1072 (1974)).

When the vector is derived from λ phage, λ phage particles are first formed by an in vitro packaging method (Horn, B., Methods in Enzymol., 68, 299 (1979)). Then the particles are added to a culture suspension of E. coli to obtain transduced phages with an ability to produce the NADH oxidase.

Methods for selecting transformed microorganisms containing recombinant DNA include standard methods, such as colony hybridization method for obtaining positive clones. The obtained transformants are cultured in a liquid at 37° C. and plasmids in the transformants can be obtained by known methods, such as an alkaline extraction method (Birnboim, H. C. & Doly, J., Nucleic Acids Res., 7, 1513 (1979)). The sequence of inserts in the plasmids can be determined by a dideoxy method (Sanger, F., Nickelen, S., & Colusion, A. R., Proc. Natl. Acad. Sci. 74, 5493 (1977)). A large amount of the desired hydrogen peroxide-generating NADH oxidase can be obtained by culturing the selected transformants.

The present invention is further illustrated by the following non-limitative examples.

EXAMPLES

Example 1

Cloning of a gene encoding hydrogen peroxide-generating NADH oxidase

Streptococus mutans NCIB11723 (The National Collection of Industrial and Marin Bacteria, 23 Street, Machar Drive, Aberdeen, U.K.) was cultured in a brain-heart infusion liquid medium at 37° C. for 6 hours and then centrifuged to collect the cells. The obtained cells were washed and treated with a lysozyme, N-acetylmuramidase (2000 U/ml). Then genomic DNA was isolated by a method of Saito-Miura (Saito, H. & Miura, K., Biochem. Biophys. Acta, 72, 619 (1963)). The isolated genomic DNA was dissolved in a Tris-Hcl/EDTA buffer and partially digested with Sau3A1. The digested fragments were separated by a 10 to 40% sucrose density-gradient centrifugation to obtain DNA fragments with 9 to 23 kb. The genomic DNA fragments were ligated with arms of λEMBL3 phage (Stratagene Cloning Systems, 11099 North Torry, Pines Road, La Jolla Calif. 92037, U.S.A.) by the use of T4 DNA ligase. The ligated fragments were packed in phage particles by using in vitro packaging kit (Stratagene Cloning Systems, 11099 North Torry, Pines Road, La Jolla Calif. 92037, U.S.A.). E.

coli P2392 (Stratagene Cloning Systems, 11099 North Torry, Pines Road, La Jolla Calif. 92037, U.S.A.) was infected with the phage particles.

The infected plaques of *E. coli* were screened by a plaque hybridization method with the use of synthetic probes based on the N terminal amino acid sequence of hydrogen peroxide-generating NADH oxidase. A positive clone hybridizing with the synthetic probes was selected.

Example 2

Preparation of a transformant including a gene encoding hydrogen peroxide-generating NADH oxidase The positive clone obtained in Example 1 was also reacted with an antibody directed to the hydrogen peroxide-generating NADH oxidase. DNA was extracted from the positive clone and digested with BamH1 to obtain a DNA fragment with 4 kbp. The DNA fragment and plasmid pMW (a plasmid with an unique BamH1 site and an ampicillin resistance gene; Nippon-Gene, 1-29, Tonyacho, Toyama 930, Japan) digested with BamH1 were mixed and ligated by adding a T4 DNA ligase in the mixture. The mixture was used to introduce the recombinant plasmid into *E. coli* JM109 (Takara Shuzo Co., LTD., Shijo-Higashinotoin, Shimogyo-ku, Kyoto 600-91, Japan). The clone that reacted with the above-mentioned antibody was selected from the transformants.

The positive clone was cultured and centrifuged to collect the cells. After the cells were washed, the plasmid was extracted with an alkaline method. The obtained plasmid was designated as pHS19.

Example 3

The determination of the sequence of a DNA fragment including a gene encoding hydrogen peroxide-generating NADH oxidase The plasmid PHS19 obtained in Example 2 was digested with EcoR1 to obtain DNA fragments with 1 kbp and 3 kbp. The DNA fragments were ligated with plasmid PUC118 or PUC119 and used for cloning of a gene encoding hydrogen peroxide-generating NADH oxidase. A transformant including the 1 kbp DNA fragment and a transformant including the 3 kbp DNA fragment were obtained. Plasmids were extracted from both of the transformants. Deletion variants including inserts with a variety of sizes necessary for the determination of base sequences were prepared with the use of kilo sequencing deletion kit (Takara Shuzo Co., Ltd., Shijo-Higashinotoin, Shimogyo-ku, Kyoto 600-91, Japan). A DNA base sequence was determined by a dideoxy nucleotide chain termination method (Messing, J. & Vieira, J., Gene, 19, 269 (1982).

The obtained base sequence is given in SEQ ID NO: 1. In this base sequence, 1-278 is a non-translational region containing promoter region, and 279-1810 is a structural DNA. An amino acid sequence deduced from the structural DNA is given in SEQ ID NO: 2. The obtained amino acid sequence was shown a 54.6% homology with the NADH oxidase encoding DNA fragment derived from *Amphibacillus xylanus*(GENETYX: Amino Acid Homology Data).

Example 4

Identification of NADH binding site and FAD binding site

In an amino acid sequence of a NADH oxidase, it is presumed that binding sites for NADH, the substrate of the NADH oxidase and FAD (flavin coenzyme) contain amino acid sequence -GXXXXG-, wherein G is glycine and X may be any amino acid residue (Ho-Jin PARK, et. al., Eur. J. Biochem., 205, 875–879(1992)). The amino acid sequence given in SEQ ID NO: 2, obtained in above Example 3 was analyzed and find two sites having the sequences corresponding to -GXXXXG-. Therefore, we assumed one of which is a NADH binding site and the another is a FAD binding site.

A NADH binding site of the NADH oxidase derived from *Amphibacilius xylanus* contains an amino acid sequence of -GGGPAG- (Gly Gly Gly Pro Ala Gly), and a FAD binding site contains -GGGNSG- (Gly Gly Gly Asn Ser Gly)(N-imura, Y. et. al.: Annual Meeting of Japanese Society of Agricultural Chemistry (1992)).

Compared with both of the NADH and FAD binding sites of the NADH oxidase of *Amphibacillus xylanus,* 215–220 of SEQ ID NO: 2 is same as the sequence of the NADH binding site, and 354–359 is same as that of FAD binding site. Therefore, it is concluded that in the SEQ ID NO. 2, the regions of 215–220 and 354–359 are each corresponding to a NADH binding site and a FAD binding site of the NADH oxidase.

Accordingly, it is concluded that 921–938 of SEQ ID NO:1 is the region encoding the NADH binding site and 1338–1355 is that encoding the FAD binding site.

What is claimed is:

1. A DNA molecular comprising nucleotides 279 through 1809 of sequence I.D. No. 1, wherein the molecule has the following base sequence:

AT GGCATTAGAC GCAGAAATCA AAGAGCAGTT AGGACAGTAT CTTCAATTAC TTGAGTGTGA GATTGTTTTA CAAGCTCAAT TAAAAGACGA TGCTAATTCT CAAAAAGTTA AGGAATTTCT CCAAGAAATC GTTGCAATGT CTCCTATGAT TTCTTTAGAC GAAAAGGAAC TTCCGCGAAC ACCTAGTTTT CGCATAGCTA AAAAGGGGCA AGAATCTGGT GTTGAATTTG CTGGCTTACC CCTTGGTCAC GAATTTTACT TCGTTTATCT TGGCTCTGTT ACAGGTTTCA GGGCGTCGGC TAAGGTAGAG ACTGATATTG TCAAACGCAT TCAAGCTGTT GATGAACCTA TGCATTTTGA AACCTATGTT AGTTTGACTT GTCATAATTG TCCAGATGTT GTTCAGGCTT TCAATATCAT GTCAGTTGTT AATCCCAACA TTTCACATAC AATGGTGGAA GGTGGCATGT TTAAAGATGA AATTGAAGCT AAGGGAATTA TGTCTGTGCC AACTGTCTAT AAAGATGGAA CAGAATTTAC CTGAGGGCGT GCTAGCATAG AGCAATTACT AGACTTGATA GCAGGTCCTG TTAAAGAAGA TGCTTTTGAT GATAAAGGTG TTTTTGATGT CCTTGTTATT GGTGGGGGTC CTGCTGGTAA TAGCGCGGCT ATCTATGCTG CAAGAAAGGG AGTTAAAACA GGACTTTTAG CTGAAACCAT GGGTGGTCAA GTTATGGAAA CCGTGGGTAT TGAAAATATG ATCGGTACCC CATATGTTGA AGGACCCCAA TTAATGGCTC AGGTGGAAGA GCATACCAAG TCTTATTCTG TTGACATCAT GAAGGCACCG CGTGCTAAGT CTATTCAAAA GACAGACTTG GTTGAAGTTG AACTTGATAA TGGAGCTCAT TTGAAAGCAA AGACAGCTGT TTTGGCCTTA GGTGCCAAGT GGCGTAAAAT CAATGTACCA GGAGAAAAAG AATTCTTTAA TAAAGGTGTT ACTTACTGTC CGCACTGTGA TGGTCCTCTT TTCACAGACA AAAAAGTCGC TGTCATTGGC GGTGGAAACT CAGGTTTAGA AGCAGCTATT GATTTGGCTG GGTTAGCTAG CCATGTCTAT ATTTTAGAAT TTTTACCTGA GTTAAAAGCT GATAAGATCT TACAAGATCG TGCGGAAGCT CTTGATAATA TTACCATTGT AACTAATGTT GCGACTAAAG AAATTATTGG CAATGACCAC GTAGAAGGTC TTCGTTACAG TGATCGTACG ACCAATGAAG AGTACTTGCT TGATTTAGAA GGTGTTTTTG TTCAAATTGG ATTGGTACCT AGTACTGACT GGTTAAAGGA TAGTGGACTA GGACTCAATG AAAAAGGTGA AATCATTGTT GCTAAAGATG GCGCAACTAA TATTCCTGCT ATTTTTGCAG CTGGTGATTG CACAGATAGT GCCTACAAAC AAATTATCAT TTCCATGGGT TCTGGAGCTA CTGCGGCTTT AGGTGCCTTT GATTATTTGA TTAGAAATT/.

2. A DNA molecule comprising the amino acid sequence I.D. No. 2, wherein the molecule encodes the following amino acid sequence:

| | | | | | | | | | | | | | | | |
|---|---|---|---|---|---|---|---|---|---|---|---|---|---|---|---|
| Met | Ala | Leu | Asp | Ala | Glu | Ile | Lys | Glu | Gln | Leu | Gly | Gln | Tyr | Leu | 15 |
| Gln | Leu | Leu | Glu | Cys | Glu | Ile | Val | Leu | Gln | Ala | Gln | Leu | Lys | Asp | 30 |
| Asp | Ala | Asn | Ser | Gln | Lys | Val | Lys | Glu | Phe | Leu | Gln | Glu | Ile | Val | 45 |
| Ala | Met | Ser | Pro | Met | Ile | Ser | Leu | Asp | Glu | Lys | Gln | Leu | Pro | Arg | 60 |
| Thr | Pro | Ser | Phe | Arg | Ile | Ala | Lys | Lys | Gly | Gln | Glu | Ser | Gly | Val | 75 |
| Glu | Phe | Ala | Gly | Leu | Pro | Leu | Gly | His | Glu | Phe | Tyr | Phe | Val | Tyr | 90 |
| Leu | Gly | Ser | Val | Thr | Gly | Phe | Arg | Ala | Ser | Ala | Lys | Val | Glu | Thr | 105 |
| Asp | Ile | Val | Lys | Arg | Ile | Gln | Ala | Val | Asp | Glu | Pro | Met | His | Phe | 120 |
| Glu | Thr | Tyr | Val | Ser | Leu | Thr | Cys | His | Asn | Cys | Pro | Asp | Val | Val | 135 |
| Gln | Ala | Phe | Asn | Ile | Met | Ser | Val | Val | Asn | Pro | Asn | Ile | Ser | His | 150 |
| Thr | Met | Val | Glu | Gly | Gly | Met | Phe | Lys | ASp | Glu | Ile | Glu | Ala | Lys | 165 |
| Gly | Ile | Met | Ser | Val | Pro | Thr | Val | Tyr | Lys | Asp | Gly | Thr | Glu | Phe | 180 |
| Thr | Ser | Gly | Arg | Ala | Ser | Ile | Glu | Gln | Leu | Leu | Asp | Leu | Ile | Ala | 195 |
| Gly | Pro | Leu | Lys | Glu | Asp | Ala | Phe | Asp | Asp | Lys | Gly | Val | Phe | Asp | 210 |
| Val | Leu | Val | Ile | Gly | Gly | Gly | Pro | Ala | Gly | Asn | Ser | Ala | Ala | Ile | 225 |
| Tyr | Ala | Ala | Arg | Lys | Gly | Val | Lys | Thr | Gly | Leu | Leu | Ala | Glu | Thr | 240 |
| Met | Gly | Gly | Gln | Val | Met | Glu | Thr | Val | Gly | Ile | Glu | Asn | Met | Ile | 255 |
| Gly | Thr | Pro | Tyr | Val | Glu | Gly | Pro | Gln | Leu | Met | Ala | Gln | Val | Glu | 270 |
| Glu | His | Thr | Lys | Ser | Tyr | Ser | Val | Asp | Ile | Met | Lys | Ala | Pro | Arg | 285 |
| Ala | Lys | Ser | Ile | Gln | Lys | Thr | Asp | Leu | Val | Glu | Val | Glu | Leu | Asp | 300 |
| Asn | Gly | Ala | His | Leu | Lys | Ala | Lys | Thr | Ala | Val | Lue | Ala | Lue | Gly | 315 |
| Ala | Lys | Trp | Arg | Lys | Ile | Asn | Val | Pro | Gly | Glu | Lys | Glu | Phe | Phe | 330 |
| Asn | Lys | Gly | Val | Thr | Tyr | Cys | Pro | His | Cys | Asp | Gly | Pro | Leu | Phe | 345 |
| Thr | Asp | Lys | Lys | Val | Ala | Val | Ile | Gly | Gly | Gly | Asn | Ser | Gly | Leu | 360 |
| Glu | Ala | Ala | Ile | Asp | Leu | Ala | Gly | Leu | Val | Ala | Ser | His | Val | Tyr | Ile | 375 |
| Leu | Glu | Phe | Leu | Pro | Glu | Leu | Lys | Ala | Asp | Lys | Ile | Leu | Gln | Asp | 390 |
| Arg | Ala | Glu | Ala | Lue | Asp | Asn | Ile | Thr | Ile | Leu | Thr | Asp | Val | Ala | 425 |
| Thr | Lys | Glu | Ile | Ile | Gly | Asn | Asp | His | Val | Glu | Gly | Leu | Arg | Tyr | 420 |
| Ser | Asp | Arg | Thr | Thr | Asn | Glu | Glu | Tyr | Leu | Leu | Asp | Leu | Glu | Lys | 435 |
| Val | Phe | Val | Gln | Ile | Gly | Leu | Val | Pro | Ser | Thr | Asp | Trp | Leu | Lys | 450 |
| Asp | Ser | Gly | Leu | Ala | Leu | Asn | Glu | Lys | Gly | Glu | Ile | Ile | Val | Ala | 465 |
| Lys | Asp | Gly | Ala | Thr | Asn | Ile | Pro | Ala | Ile | Phe | Ala | Ala | Gly | Asp | 480 |
| Cys | Thr | Asp | Ser | Ala | Tyr | Lys | Gln | Ile | Ile | Ile | Ser | Met | Gly | Ser | 495 |
| Lys | Ala | Thr | Ala | Ala | Leu | Gly | Ala | Phe | Asp | Tyr | Leu | Ile | Arg | Asn | 510 |

3. A DNA molecule wherein the 5' terminal non-translated region comprises the following base sequence:

| | | | | | | |
|---|---|---|---|---|---|---|
| GGATCCCTTC | TCATGTTCTC | TCACAAGGAT | TTGAGGTTTT | AGGTGAAGAT | GGTTTAGCAC | 60 |
| AACGTGGAAC | CTTTATTGTA | GATCCGGATG | GTATCATTCA | AATGATGGAA | GTCAATGCAG | 120 |
| ATGGTATTGG | TCGTGATGCT | ACTACCTTGA | TTGATAAAGT | TGTGCAGCT | CAATCTATTC | 180 |
| GCCAACATCC | AGGAGAAGTT | TGCCCTGCCA | AATGGAAAGA | GGGAGCTGAA | ACTTTAAAAC | 240 |
| CAAGTTTGGT | ACTTGTCGGT | AAAATTTAAG | GAGAAACT. | | | |

4. A plasmid including a DNA molecule encoding an NADH oxidase according to claim 1.

5. A plasmid including a DNA molecule encoding an NADH oxidase according to claim 2.

* * * * *